United States Patent [19]

McKittrick et al.

[11] Patent Number: 4,785,015

[45] Date of Patent: Nov. 15, 1988

[54] SUBSTITUTED 1,3,4,9-TETRAHYDROPYRANO [3,4-B]INDOLE-1-ACETIC ACIDS

[75] Inventors: Brian A. McKittrick, Bloomfield; Alan H. Katz, Lawrenceville, both of N.J.

[73] Assignee: American Home Products Corporation, New York, N.Y.

[21] Appl. No.: 117,775

[22] Filed: Nov. 5, 1987

[30] Foreign Application Priority Data

Feb. 20, 1987 [CA] Canada .................................. 530253

[51] Int. Cl.$^4$ .................. C07D 491/052; A61K 31/40
[52] U.S. Cl. ...................................... 514/411; 548/432
[58] Field of Search ......................... 548/432; 514/411

[56] References Cited

U.S. PATENT DOCUMENTS 3,939,178 2/1976 Demerson .......................... 548/432

Primary Examiner—Alan L. Rotman
Assistant Examiner—Robert C. Whittenbaugh
Attorney, Agent, or Firm—Walter Patton

[57] ABSTRACT

Indole derivatives characterized by having a 1,3,4,9-tetrahydropyrano[3,4-b]indole-1-acetic acid nucleus bearing a substituent in position 1-, 4-, 5-, 6-, 7- and 8- are disclosed. The derivatives are useful anti-inflammatory and analgesic agents and methods for their preparation and use are also disclosed.

7 Claims, No Drawings

SUBSTITUTED 1,3,4,9-TETRAHYDROPYRANO [3,4-B]INDOLE-1-ACETIC ACIDS

BACKGROUND OF THE INVENTION a. Field of Invention

This invention relates to novel indole derivatives, and to the processes for their preparation and use.

Notwithstanding the advances made during the last four decades in the development of agents for the treatment of inflammatory conditions and for analgesic purposes in conditions which require relief from pain in a mammal, there still remains a need for effective agents without the side effects associated with the therapeutic agents presently used for these purposes.

More specifically, this invention relates to tricyclic acetic acid derivatives in which the tricyclic portion thereof is characterized by having an indole portion fused to a pyrano ring. Still more specifically, the compounds of this invention are characterized as derivatives of the following tricyclic acetic acid system:

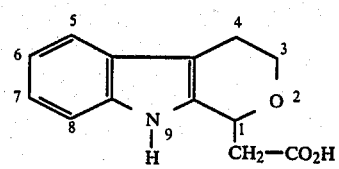

1,3,4,9-tetrahydropyrano[3,4-b]indole-1-acetic acid in which the carbons at the 1-, 4-, 5-,6-, 7-, and 8-positions are further substituted.

The indole derivatives of this invention have been found to exhibit useful pharmacodynamic properties without eliciting undesirable side effects. Notable attributes of this effect are anti-inflammatory and analgesic activities.

b. Prior Art

The closest prior art to the present invention is:

Demerson et al, U.S. Pat. No. 3,939,178. Demerson et al disclosed 1,3,4,9-tetrahydropyrano[3,4-b]indoles and 1,3,4,9-tetrahydrothiopyrano[3,4-b]indoles having analgesic and anti-inflammatory activity but not with the substituents of the present invention. Hughes et al, U.S. Ser. No. 876,552, filed June 19, 1986. Related U.S. Patents are U.S. Pat. Nos. 3,974,179; 3,843,681 and U.S. Ser. No. 838,510, filed Mar. 11, 1986.

SUMMARY OF THE INVENTION

The compounds of this invention are represented by formula (I)

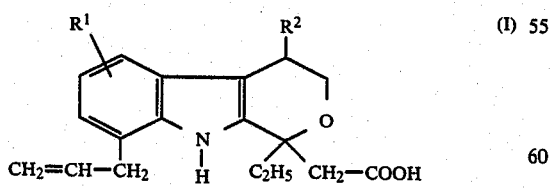

wherein $R^1$ is hydrogen, lower alkyl containing 1 to 4 carbon atoms or halogen, $R^2$ is hydrogen or lower alkyl containing 1 to 4 carbon atoms and the pharmaceutically acceptable salts thereof.

A preferred aspect of the present invention is the compounds represented by formula (I) wherein $R^1$ is hydrogen or fluorine and $R^2$ is hydrogen or methyl and the pharmaceutically acceptable salts thereof.

The most preferred compounds of the present invention are designated 1-ethyl-7-fluoro-1,3,4,9-tetrahydro-8-(2-propenyl)-pyrano[3,4-b]indole-1-acetic acid;

1-ethyl-1,3,4,9-tetrahydro-8-(2-propenyl)-pyrano[3,4-b]-1-acetic acid; and 1-ethyl-1,3,4,9-tetrahydro-4-methyl-8-(2-propenyl)-pyrano[3,4-b]indole-1-acetic acid (Isomer A).

The indole derivatives of this invention of formula (I) are prepared by the following processes.

Process 1

[Reaction scheme showing synthesis steps starting from substituted aniline $R^1$–C$_6$H$_4$–NH$_2$, through trifluoroacetamide intermediate, halogenated aniline hydrochloride (X = Br or I), hydrazine intermediate, substituted indole with tryptophol, methyl ester intermediate, and final acetic acid product]

wherein $R^1$ is as defined above

Process 2

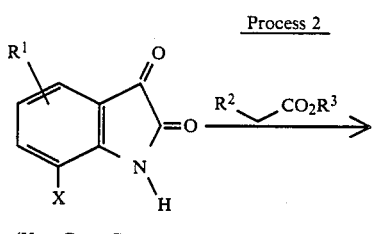

(X = Br or I)

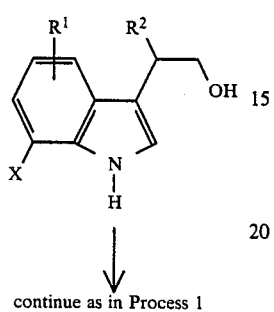

continue as in Process 1 wherein $R^1$ and $R^2$ are as defined above and $R^3$ is methyl or ethyl.

DETAILED DESCRIPTION OF THE INVENTION

The term "lower alkyl" as used herein represents straight chain alkyl radicals containing 1 to 4 carbon atoms and branched chain alkyl radicals containing three to four carbon atoms and includes methyl, ethyl, propyl, isopropyl, butyl, isobutyl and the like.

The term "halogen" as used herein includes fluorine, chlorine, bromine and iodine.

The compounds of formula (I) form salts with suitable pharmaceutically acceptable inorganic and organic bases. These derived salts possess the same activities as the parent acid and are included within the scope of this invention. The acid of formula (I) is transformed in excellent yield into the corresponding pharmaceutically acceptable salts by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. The preferred salt is the sodium salt. Suitable organic bases include the following amines; lower mono-, di- and tri-alkylamines, the alkyl radicals of which contain up to three carbon atoms, such as methylamine, dimethylamine, trimethylamine, ethylamine, di- and triethylamine, methylethylamine, and the like; mono, di- and trialkanolamines, the alkanol radicals of which contain up to three carbon atoms, such as mono-, di- and triethanolamine; alkylenediamines which contain up to six carbon atoms, such as hexamethylenediamine; amino sugars, such as glucosamine; cyclic saturated or unsaturated bases containing up to six carbon atoms, such as pyrrolidine, piperidine, morpholine, piperazine and their N-alkyl and N-hydroxyalkyl derivatives, such as N-methylmorpholine and N-(2-hydroxyethyl)piperidine, as well as pyridine. Furthermore, there may be mentioned the corresponding quaternary salts, such as the tetraalkyl (for example tetramethyl), alkyl-alkanol (for example methyltrimethanol and trimethyl-monoethanol) and cyclic ammonium salts, for example the N-methyl-pyridinium, N-methyl-N-(2-hydroxyethyl)-morpholinium, N,N-dimethyl-morpholinium, N-methyl-N-(2-hydroxyethyl)morpholinium, N,N-dimethyl-piperidinium salts, which are characterized by good water-solubility. In principle, however, there can be used all the ammonium salts which are physiologically compatible.

The transformations to the salts can be carried out by a variety of methods known in the art. For example, in the case of salts of inorganic bases, it is preferred to dissolve the acid of formula (I) in water containing at least one equivalent amount of a hydroxide, carbonate, or bicarbonate. Advantageously, the reaction is performed in a water-miscible organic solvent inert to the reaction conditions, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid salt if that form is desired.

To produce an amine salt, the acid of formula (I) is dissolved in a suitable solvent of either moderate or low polarity, for example, ethanol, acetone, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

Also included in this invention are the optical isomers of the compounds of formula (I) which result from asymmetric centers, contained therein e.g. 1-carbon. Such isomers can be obtained in substantially pure form by classical separation techniques and by stereochemically controlled syntheses. Included is the specific case of the resolution of 1-ethyl-1,3,4,9-tetrahydropyrano[3,4-b]indole-1-acetic acids into their optical isomers by separation of the corresponding [(1S)-endo]-1,7,7-trimethyl-bicyclo[2.2.1]heptan-2-yl esters followed by basic hydrolysis.

ANTI-INFLAMMATORY ACTIVITY

The useful anti-inflammatory activities of the pyranoindole acetic acid derivatives of formula (I) are demonstrated in standard pharmacologic tests, for example, the test designated: Preventative Adjuvant Edema The objective of this test is to determine the ability of test drugs to exhibit an acute anti-inflammatory effect in rats. This test is a primary screen for anti-inflammatory drugs.

Species:

Male Sprague Dawley rats (180–200 g) are used. The animals have free access to water but food is withdrawn 18 hours before testing.

Drug Preparations and Administration:

Freund's complete adjuvant is prepared by suspending 5 mg of killed and dried *Mycobacterium butyricum* (Difco) in 1 mL mineral oil. The test compounds are dissolved, or suspended in 0.5% Tween 80 in distilled water according to their solubility. For primary screening all drugs are administered by gastric lavage at the arbitrary dosage of 25 mg/kg, p.o. in a volume of 0.5 mL/100 g body weight to groups of 10 animals.

Methodological Details:

The method is essentially that described by Wax et al, J. Pharmacol. Exp. Ther., 192, 166–171 (1975). Groups of rats are injected intradermally in the left hind paw with 0.1 mL of Freund's complete adjuvant. The test compound or vehicle is administered immediately before the adjuvant, 24 hours and 48 hours after the adjuvant (days 0, 1 and 2). The injected hind paw volume is measured before the injection of adjuvant and 24 hrs. after the last drug administration (day 3) by means of a plethysmometer (Buxco Electronics Inc.) The difference between the hind paw volume on day 0 and day 3 represents the edema volume. Etodolac (25 mg/kg, p.o.) is included as a positive control.

Presentation of Results:

The mean edema volume (expressed as mL±SEM) is calculated for each group and the percentage protection conferred by the drug is calculated:

$$\% \text{ protection} = \frac{(c-t)\,100}{c}$$

where c is the mean edema volume for the vehicle-treated (0.5% Tween 80 in distilled water) controls and t is the mean edema volume for the drug treated group.

ANALGESIC ACTIVITY

A further test used to determine the utility of the compounds of the present invention is designated: Drug Effects on Phenylbenzoquinone-induced Writhing in Mice The objective of this test is to determine the ability of test drugs to inhibit the nociceptive (pain) response of mice injected with a chemical irritant. This test is a primary screen for both peripheral and centrally acting analgesic drugs.

Species:

Male Swiss albino mice (15–25 g). The animals are fasted for 18 hours prior to use but have free access to water.

Drug Preparation and Administration:

Drugs are dissolved or suspended according to their solubility in 0.5% Tween 80 in distilled water. They are administrated by gastric gavage in a volume of 5 mL/kg. For primary screening all drugs are administered at the arbitary dosage of 25 mg/kg, p.o. to a group of 10 mice.

Methodological Details:

A modification of the method of Siegmund et al, Proc. Soc. Exp. Biol. Med., 95, 729–731 (1957) is used. Groups of 5 mice are dosed with the test compound or vehicle control. Sixty minutes later the animals are injected i.p. with 0.3 mL/20 g body weight of a 0.02% solution of phenylbenzoquinone (PBQ; 2-phenyl-1,4-benzoquinone) and placed in individual observation boxes. The number of writhing or abdominal squirming movements made by each mouse during the following 15 min. period is counted. The experiment is repeated with another group of 5 mice and the mean number of writhes per mouse for a group of 10 mice is calculated.

Presentation of Results:

Drug treated and vehicle-treated control groups are compared and the percentage protection conferred by the drug is calculated:

$$\text{Percentage protection} = \frac{(c-t)\,100}{c}$$

where c = mean number of writhes in the control group
where t = mean number of writhes in the test drug group An additional test used to determine the utility of the compounds of the present invention is designated: Randall Selitto Test in the Rat The objective of this test is to assess the potency of peripheral and central acting drugs in inhibiting the reaction of rats to painful stimulation applied to an inflamed paw.

Species:

Male Sprague Dawley rats (180–200 g) are used. The animals are fasted overnight prior to drug administration.

Drug Preparation and Administration:

Freund's Complete Adjuvant (FCA) is prepared by suspending 5 mg killed and dried mycobacterium butyricum (Difco) in 1 mL mineral oil. The test compounds are dissolved or suspended in 0.5% Tween 80 in distilled water according to their solubility. They are administered by gastric gavage in a volume of 0.5 mL/100 g body weight to groups of 10 animals.

Methodological details:

Ten rats are used per group. The method is essentially that described by Randall and Selitto, Arch. Int. Pharmacodyn. 111, 409 (1957) and the apparatus which is used to apply pressure to the paw (Analgesi-meter for the rat paw, Ugo Basile, Comeria, Italy) is a modification of that described by Gilfoil et al, J. Pharmacol. 142, 1 (1963). The instrument is basically a device which exerts a force that increases at a constant rate. The force is continuously monitored by a pointer moving along a linear scale and is measured in grams. The inflammatory reaction is induced in the left hind paw of rats by injecting 0.1 mL of Freund's adjuvant intradermally. The test compound or vehicle is administered 24 hours after the adjuvant. The pain threshold (vocalization) is determined 1 hour later in the inflamed paw of the treated and control groups.

Presentation of Results and Criteria for Activity:

Each animal which has a reading 1.5 times greater than the mean reading of the control-group will be considered as responsive (having an analgesic effect) to treatment. The number of animals showing an analgesic effect is then determined in each group.

The $ED_{50}$ (dose which causes analgesia in 50% of the animals) using at least 3 doses is then determined, by the method described in Litchfield and Wilcoxon, J. Pharmacol. Exp. Ther., 96, 99–113 (1949).

Typical results obtained for the compounds of the present invention in the aforementioned tests are as follows:

TABLE I

Substituted 1,3,4,9-Tetrahydropyrano[3,4-b]indole-1-acetic Acids

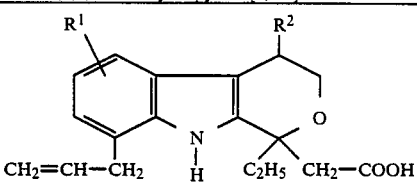

| Example | Preventative Adjuvant Edema* | Phenylquinone Writhing in Mice* | Randall Selitto |
|---|---|---|---|
| 1 | 83(25) | 54.7 | 0.7 |
| 2 | 9 | 42(200) | — |
| 3 | 57(25) | 20(10) | — |

*The numbers quoted are either percent inhibition at the dose in mg/kg given in parentheses or the $ED_{50}$ in mg/kg. See Table II for definitions of $R^1$ and $R^2$.

The lack of side effects associated with the compounds of this invention are demonstrated by standard acute toxicity tests as described by R. A. Turner in "Screening Methods in Pharmacology," Academic Press, New York and London, 1965, pp. 152–163, and by prolonged administration of the compound to warm-blooded animals.

When the compounds of this invention are employed as anti-inflammatory and analgesic agents in warm-blooded animals, they are administered orally, alone or in dosage forms, i.e., capsules or tablets, combined with pharmacologically acceptable excipients, such as starch, milk sugar and so forth, or they are administered orally in the form of solutions in suitable vehicles such as vegetable oils or water. The compounds of this invention may be administered orally in sustained release dosage form or transdermally in ointments or patches. The compounds of this invention may also be administered in the form of suppositories.

The dosage of the compounds of formula (I) of this invention will vary with the particular compound chosen and form of administration. Furthermore, it will vary with the particular host under treatment. Generally, the compounds of this invention are administered at a concentration level that affords efficacy without any deleterious side effects. These effective anti-inflammatory and analgesic concentration levels are usually obtained within a therapeutic range of 1.0 μg to 500 mg/kg per day, with a preferred range of 1.0 μg to 100 mg/kg per day. The preferred anti-inflammatory and analgesic dose range is 20 μg to 20 mg/kg/day.

The compounds of this invention may be administered in conjunction with nonsteroidal anti-inflammatory drugs such as acetaminophen, ibuprofen and aspirin and/or with opiate analgesics such as codeine, oxycodone and morphine together with the usual doses of caffeine. When used in combination with other drugs, the dosage of the compounds of the present invention is adjusted accordingly.

The compounds of the present invention also possess antipyretic activity.

The following examples further illustrate this invention.

EXAMPLE 1

1-Ethyl-7-fluoro-1,3,4,9-tetrahydro-8-(2-propenyl)-pyrano[3,4-b]indole-1-acetic Acid (I, $R^1$=7-fluoro, $R^2$=—H)

Step 1. Preparation of 3-Fluoro-trifluoroacetanilide

According to the procedure of P. A. Wender, et al, Tet. 39, 3767 (1983), trifluoroacetic anhydride (125 mL, 0.819 mol) was added dropwise to a stirred mixture of sodium carbonate (120 g, 1.13 mol) and 3-fluoroaniline (75.2 g, 0.677 mol) in 500 mL ether at 10° C. After 1 hour, hexane (200 mL) was added and the sodium carbonate filtered off. The solution was washed with ice water, 10% aqueous NaHCO₃ and then brine. The ethereal solution was charcoalized, dried (MgSO₄) and concentrated to yield 160 g of a tan solid. The solid was suspended in hot petroleum ether (500 mL), cooled and filtered to give 116 g (82.7%) of 3-fluoro-trifluoroacetanilide.

Step 2. Preparation of 2-Bromo-3-fluoroaniline

A solution of t-butyllithium in pentane (75 mL, 1.6 mol) was added to TMEDA (18 mL, 0.119 mol) in THF (~200 mL) at −78° C. After stirring for 10 minutes a precooled solution of 3-fluoro-trifluoroacetanilide (11.6 g, 0.056 mol) in THF (100 mL) was added dropwise via cannula addition over 20 minutes (temperature kept below −65° C. during addition). After stirring for 1 hour at −75° C., bromine (3.4 mL, 0.067 mol) was then added over 5 minutes. This mixture was stirred at −70° C. for 1 hour, the temperature raised to −45° C. and continued for an additional 30 minutes. The reaction was quenched by addition of 2N HCl (pH 6) and sodium thiosulfate, then extracted with ether. The ether layers were washed with brine and then concentrated to yield an amber oil (10 g). This oil was dissolved in ethanol (100 mL) and 1N KOH (120 mL) added. the mixture was heated to reflux for 1 hour, then cooled and concentrated to remove the ethanol. The residue was extracted with ether. Concentration of the ether gave a mobile liquid which was purified via flash chromatography using 1:4 EtOAc:hexane to give the desired 2-bromo-3-fluoroaniline as a liquid. The liquid was dissolved in petroleum ether-ether 1:1 and ethereal HCl added. The white precipitate (6.0 g) (47%) was collected by filtration and dried in vacuo at room temperature.

¹H NMR (CDCl₃) free base: δ7.05 (q, 1H, J=7.5 Hz), 6.52 (m, 2H), 4.20 (2H).

Step 3. Preparation of 7-Bromo-6-fluorotryptophol

An aqueous solution of sodium nitrite (2.0 g, 0.029 mol in 6.5 mL H₂O) was added dropwise over 30 minutes to a 0° C. suspension of 3-fluoro-2-bromoaniline hydrochloride (6.0 g, 0.0265 mol) in aqueous HCl (9.3 mL concentrated HCl+6.5 mL H₂O). After 1 hour at this temperature, a HCl solution (15 mL, 6N HCl) of stannous chloride dihydrate (12.5 g, 0.0554 mol) was added dropwise over 45 minutes and stirring continued an additional 3 hours at 0° C. The mixture was basified with 50% NaOH (pH 14) and extracted with ether. The ether layers were washed with brine, dried over MgSO₄, and concentrated. The residue was dissolved in 1:1 petroleum ether-ether and technical grade HCl gas introduced. The tan precipitate was collected by filtration, washed with Et₂O/petroleum ether and dried in vacuo to yield the hydrazine hydrochloride (3.2 g) (50%). This material was dissolved in 10% aqueous THF (40 mL) and a solution of dihydrofuran (1.0 g, 0.0143 mol) in THF (5 mL) added at 0° C. This mixture was stirred at −10° C. to room temperature over 2 hours. Ether was added to the reaction mixture and the organic phase washed with brine. Concentration of the ether layer afforded the hydrazone (3.7 g as an amber oil). Without further purification the hydrazone (3.6 g, 0.0131 mol) was suspended in ethylene glycol (15 mL)

and zinc chloride (3.6 g, 0.03 mol) added. This mixture was heated to 165°–170° C. for 6 hours, then cooled to room temperature and extracted with ether. The ether layers were washed (brine), dried (MgSO$_4$) and concentrated to yield an oil. This was purified via flash chromatography using 1:2 EtOAc:hexane to give the tryptophol as a light yellow oil (1.12 g) (16.4%).

$^1$H NMR (CDCl$_3$): δ8.25 (broad s, 1H), 7.46 (dd, 1H, 5 Hz), 7.13 (d, 1H, 1.5 Hz), 6.95 (t, 1H, 8.5 Hz), 3.90 (bt, 2H, 6 Hz), 3.01 (t, 2H, 6 Hz).

Step 4. Preparation of 8-Bromo-1-ethyl-7-fluoro-1,3,4,9-tetrahydropyrano[3,4-b]indole-1-acetic Acid, Methyl Ester 7-Bromo-6-fluorotryptophol (1.1 g, 0.0043 mol) was dissolved in CH$_2$Cl$_2$ (60 mL). To this was added methyl 3-methoxy-2-pentenoate (0.65 g, 0.005 mol) and borontrifluoride etherate (0.2 mL). After stirring at room temperature for 40 minutes the mixture was diluted with 10% NaHCO$_3$. The CH$_2$Cl$_2$ layer was separated and dried (MgSO$_4$) to yield 1.6 g (100%) of the pyrano[3,4-b]indole product as an oil.

$^1$H NMR (CDCl$_3$): δ9.35 (broad s, 1H), 7.33 (q, 1H, J=9.8 Hz), 6.91 (t, 1H, J=8.5 Hz), 4.00 (m, 2H), 3.78 (s, 3H), 2.95 (q, 2H, J=16 Hz), 2.75 (m, 2H), 2.08 (m, 2H), 0.82 (t, 3H, J=7 Hz).

Step 5. Preparation of 1-Ethyl-7-fluoro-1,3,4,9-tetrahydro-8-(2-propenyl)pyrano[3,4-b]indole-1-acetic Acid According to the procedure of Kosugi et al, Chem. Letters 301 (1977) tetrakis-(triphenylphosphine) palladium [O] (60 mg) was added to a mixture of tributylallyltin (1.75 g, 0.0053 mol) and 8-bromo-1-ethyl-7-fluoro-1,3,4,9-tetrahydro-pyrano[3,4-b]indole-1-acetic acid, methyl ester (1.6 g, 0.0043 mol) in benzene (4.0 mL) under N$_2$. The sealed tube was then heated to 80° C. for 15 hours, more palladium catalyst was added (30 mg), and heating continued for 42 hours at 110°–120° C. The cooled reaction mixture was diluted with Et$_2$O, then filtered through a glass wool plug. The ether was washed twice with brine, then dried (MgSO$_4$) to yield an oil that was purified via flash chromatography. Using 1:7 EtOAc:hexane to afford 1.12 g, (~78%) of 1-ethyl-7-fluoro-1,3,4,9-tetrahydro-8-(2-propenyl)-pyrano[3,4-b]indole-1-acetic acid, methyl ester as a colorless oil. The oil was dissolved in ethanol (40 mL) and 1N sodium hydroxide added (15 mL). The mixture was heated to reflux for 2 hours then cooled and concentrated. 1N HCl was added and the aqueous solution extracted with ether. The ether layers were washed (brine), dried (MgSO$_4$) and concentrated to yield a foamy oil. This was purified by flash chromatography on SiO$_2$-pretreated with 2% H$_3$PO$_4$-MeOH. Using 1:2 EtOAc:hexane to give 1 g (73%) of 1-ethyl-7-fluoro-1,3,4,9-tetrahydro-8-(2-propenyl)-pyrano[3,4-b]indole-1-acetic acid as a colorless oil which crystallized from toluene:petroleum ether, m.p. 123°–125° C.

EXAMPLE 2

1-Ethyl-1,3,4,9-tetrahydro-8-(2-propenyl)-pyrano[3,4-b]-1-acetic Acid (I, R$^1$=—H, R$^2$=—H)

The compound is prepared by the process of Example 1, starting with 2-bromoaniline to give the product of m.p. 97°–100° C.

EXAMPLE 3

1-Ethyl-1,3,4,9-tetrahydro-4-methyl-8-(2-propenyl)-pyrano[3,4-b]indole-1-acetic Acid (I, R$^1$=—H, R$^2$=—CH$_3$)

Step 1. Preparation of β-Methyl-7-bromotryptophol

To a solution of lithium diisopropylamine (LDA) in tetrahydrofurancyclohexane (220.0 mL, 0.44 mol, 2.0 M) and 400 mL of dry THF, cooled to −78° C. under a nitrogen atmosphere, was added a solution of ethyl propionate (40.85 g, 0.40 mol) in 150 mL of dry THF. The solution was allowed to stir for 30 minutes, maintaining temperature at −70° C. A solution of 7-bromoisatin (42.40 g, 0.20 mol) in 250 mL of dry THF was added dropwise and the mixture was warmed to room temperature and then heated at reflux for 0.5 hours. The reaction mixture was cooled to room temperature and quenched with 200 mL of saturated ammonium chloride solution. The aqueous layer was removed and the organic layer was washed with 200 mL of water, dried over MgSO$_4$, filtered and concentrated to give 25.5 g of a red brown oil. This material was dissolved in 250 mL of dry THF and added to a cooled (0° C.) mixture of lithium aluminum hydride (15.18 g, 0.40 mol) in 700 mL of dry THF. The mixture was stirred at room temperature for 20 hours and then cooled in an ice bath. 1N HCl solution (300 mL) was added dropwise and the salts were removed by filtration and washed with ether. The organic layer was separated from the filtrate and dried over MgSO$_4$, filtered and concentrated to give 57.12 g of a brown oil, used in the next step without further purification.

Step 2. Preparation of 8-Bromo-1-ethyl-1,3,4,9-tetrahydro-4-methylpyrano[3,4-b]indole-1-acetic Acid, Methyl Ester A mixture of β-methyl-7-bromotryptophol (57.12 g), methyl 3-methoxy-2-pentenoate (35.60 g, 0.24 mol), and BF$_3$.Et$_2$O (7.5 mL) in 700 mL of methylene chloride was stirred at room temperature overnight. Saturated NaHCO$_3$ solution (125 mL) was added to the mixture. The organic layer was washed with 200 mL of water, dried over MgSO$_4$, filtered and concentrated to afford 21.03 g of a dark brown oil. This material was purified by flash chromatography (10% EtOAc-hexane, silica gel) to give the pure product as a pale yellow oil (5.25 g, 7.2% yield based on 7-bromoisatin).

IR (KBr) 3360, 1710 cm$^{-1}$.

$^1$H NMR (CDCl$_3$) δ9.28 (s, 1H), 7.53 (d, 1H, J=7.9), 7.31 (d, 1H, J=7.6), 6.97 (t, 1H, J=7.8), 3.99 (dd, 1H, J=11.4, 4.4), 3.75 (s, 3H), 3.57 (dd, 1H, J=11.4, 5.7), 3.09 (m, 1H), 2.98 (s, 2H), 2.08 (m, 2H), 1.34 (d, 3H, J=6.9), 0.85 (t, 3H, J=7.4).

Step 3. Preparation of 1-Ethyl-1,3,4,9-tetrahydro-4-methyl-8-(2-propenyl)-pyrano[3,4-b]indole-1-acetic Acid, Methyl Ester A mixture of methyl 8-bromo-1-ethyl-1,3,4,9-tetrahydro-4-methylpyrano[3,4-b]indole-1-acetate (5.21 g, 14.20 mmol), allyltributyltin (5.89 g, 17.75 mmol), tetrakis(triphenylphosphino)palladium[O] (198 mg), and 10.2 mL of benzene was heated in a sealed tube at 100° C. for 48 hours. It is important that the mixture completely fills the tube in order to obtain complete conversion. The green/yellow reaction mixture was cooled and partitioned between 60 mL of water and 120 mL of ether. The aqueous layer was removed and the organic layer was washed with 60 mL of saturated NaCl solution, dried over MgSO$_4$, filtered and concentrated to give an oil. This material was purified by flash chromatography (10% EtOAc-Hexane, silica gel) to give 2.52 g (54.2%) of pure product as a yellow oil.

IR (KBr) 3370, 1705 cm$^{-1}$.

$^1$H NMR (CDCl$_3$) δ9.09 (s,1H), 7.48 (d, 1H, J=7.7), 7.03 (t, 1H, J=7.5), 6.97 (d, 1H, J=7.0), 6.04 (m, 1H), 5.29 (d, 1H, J=17), 5.15 (d, 1H, J=10), 3.97 (dd, 1H, J=11.3, 4.3), 3.71 (s, 3H), 3.61 (d, 2H, J=6.5), 3.56 (dd, 1H, J=11.4, 5.6), 3.09 (m, 1H), 2.95 (s, 2H), 2.06 (m, 2H), 1.34 (d, 3H, J=6.8), 0.83 (t, 3H, J=3.9, 7.3).

Step 4. Preparation of 1-Ethyl-1,3,4,9-tetrahydro-4-methyl-8-(2-propenyl)-pyrano[3,4-b]indole-1-acetic Acid The 1-ethyl-1,3,4,9-tetrahydro-4-methyl-8-(2-propenyl)-pyrano[3,4-b]indole-1-acetic acid, methyl ester (2.52 g, 7.70 mmol) was added to a mixture of 125 mL of 10% aqueous sodium hydroxide and 125 mL of ethanol, and the reaction mixture was heated under reflux for 2.5 hours. The mixture was concentrated and the resulting cloudy solution was cooled, acidified with concentrated HCL, and extracted with ether (2×250 mL). The combined ether extracts were dried over MgSO$_4$, filtered and concentrated to give 2.45 g of product. This material was recystallized from toluene to give 1.45 g (57.5%) of pure product as a white solid, m.p. 153.0°–154.5° C.

IR (KBr) 3380, 1720, 1645 cm$^{-1}$.

$^1$H NMR (CDCl$_3$) δ8.59 (s, 1H), 7.45 (d, 1H, J=7.8), 7.05 (t, 1H, J=7.2, 7.8), 6.98 (d, 1H, J=6.3), 6.02 (m, 1H), 5.23 (d, 1H, J=17.1), 5.13 (d, 1H, J=10.0), 4.06 (dd, 1H, J=11.4, 4.4), 3.66 (dd, 2H, J=11.4, 5.4), 3.58 (d, 1H, J=6.6), 3.13 (m, 1H), 3.03 (s, 2H), 2.05 (m, 2H), 1.38 (d, 3H, J=6.9), 0.85 (t, 3H, J=7.4).

Anal. Calcd. for C$_{19}$H$_{23}$NO$_3$: C, 72.82; H, 7.40; N, 4.47%. Found: C, 72.98; H, 7.29; N, 4.62%

TABLE II

Substituted 1,3,4,9-tetrahydropyrano[3,4-b]indole-acetic Acids

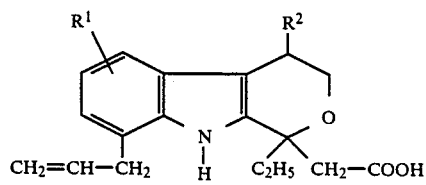

| Example | R$^1$ | R$^2$ | Melting Point °C. |
|---|---|---|---|
| 1 | 7-F | —H | 123–125 |
| 2 | —H | —H | 97–100 |
| 3 | —H | —CH$_3$ | 153–154.5 |

We claim:
1. The compounds having the structure

(I)

wherein R$^1$ is hydrogen, lower alkyl having 1 to 4 carbon atoms or halogen, R$^2$ is hydrogen or lower alkyl having 1 to 4 carbon atoms or a pharmaceutically acceptable salt thereof.

2. The compounds according to claim 1 wherein R$^1$ is hydrogen or fluorine and R$^2$ is hydrogen or methyl or a pharmaceutically acceptable salt thereof.

3. A compound according to claim 2 which is 1-ethyl-7-fluoro-1,3,4,9-tetrahydro-8-(2-propenyl)-pyrano[3,4-b]indole-1-acetic acid or a pharmaceutically acceptable salt thereof.

4. The compound according to claim 2 which is 1-ethyl-1,3,4,9-tetrahydro-8-(2-propenyl)-pyrano[3,4-b]indole-1-acetic acid or a pharmaceutically acceptable salt thereof.

5. A compound according to claim 2 which is 1-ethyl-1,3,4,9-tetrahydro-4-methyl-8-(2-propenyl)-pyrano[3,4-b]indole-1-acetic acid or a pharmaceutically acceptable salt thereof.

6. A pharmaceutical composition comprising an effective amount of a compound of structure (I), or a pharmaceutically acceptable salt thereof, as defined in claim 1 and a pharmaceutically acceptable carrier.

7. A method for treating inflamation or pain in a mammal in need which comprises the administration to said mammal of an effective amount of a compound selected from those of formula (I) of claim 1, or a pharmaceutically acceptable salt thereof.

* * * * *